(12) United States Patent
Bing et al.

(10) Patent No.: US 11,986,576 B2
(45) Date of Patent: May 21, 2024

(54) AIR FRESHENER WITH MULTIPLE AIR FLOW PATHS

(71) Applicant: Cintas Corporate Services, Inc., Cincinnati, OH (US)

(72) Inventors: Richard R. Bing, West Chester, OH (US); Megan Kathryn Helms, Hamilton, OH (US); David Steven Mesko, Wyoming, OH (US); Michael E Berger, Brooklyn, NY (US); Adem Önalan, Jersey City, NJ (US); Marco C. Perry, Brooklyn, NY (US)

(73) Assignee: Cintas Corporate Services, Inc., Cincinnati, OH (US)

( * ) Notice: Subject to any disclaimer, the term of this patent is extended or adjusted under 35 U.S.C. 154(b) by 442 days.

(21) Appl. No.: 17/499,016

(22) Filed: Oct. 12, 2021

(65) Prior Publication Data

US 2022/0133935 A1 May 5, 2022

Related U.S. Application Data

(60) Provisional application No. 63/109,894, filed on Nov. 5, 2020.

(51) Int. Cl.
*A61L 9/01* (2006.01)
*A61L 9/12* (2006.01)

(52) U.S. Cl.
CPC .............. *A61L 9/01* (2013.01); *A61L 9/12* (2013.01); *A61L 2209/134* (2013.01); *A61L 2209/15* (2013.01)

(58) Field of Classification Search
CPC .......... A61L 9/04; A61L 9/12; A61L 2209/10; A61L 2209/13; A61L 2209/134; A61L 2209/15
USPC .......................... 239/34, 44, 47, 51.5, 53–60
See application file for complete search history.

(56) References Cited

U.S. PATENT DOCUMENTS

| | | | | |
|---|---|---|---|---|
| 2,765,951 A | * | 10/1956 | Wheeler | B65D 39/0047 239/58 |
| 4,301,095 A | | 11/1981 | Mettler et al. | |
| 4,361,279 A | * | 11/1982 | Beacham | A61L 9/12 239/58 |
| 4,549,693 A | * | 10/1985 | Barlics | A61L 9/12 206/0.5 |
| 5,527,493 A | | 6/1996 | McElfresh et al. | |
| 8,097,214 B2 | * | 1/2012 | Wood | A61L 9/122 422/123 |
| 8,170,405 B2 | | 5/2012 | Harris | |
| 8,251,299 B1 | * | 8/2012 | Irvin | A61L 9/048 239/57 |
| 8,385,730 B2 | | 2/2013 | Bushman et al. | |
| 9,155,812 B1 | | 10/2015 | Bourne | |

(Continued)

*Primary Examiner* — Darren W Gorman
(74) *Attorney, Agent, or Firm* — Wood Herron & Evans LLP (57) ABSTRACT

An air-treating apparatus for dispensing a volatilizable material, such as air freshener fragrance, into the atmosphere of an enclosed area. The apparatus includes a housing and a reservoir of the volatilizable material therein, and also includes a multiple-configured air flow path arrangement which enables air-flow through the apparatus in multiple configurations. The apparatus enables use of the consistent delivery rates of a volatilizable material producing a more consistent delivery rate than normally achieved with such devices.

18 Claims, 7 Drawing Sheets

(56) References Cited

U.S. PATENT DOCUMENTS

| | | | |
|---|---|---|---|
| 9,889,220 B1 | 2/2018 | Yip et al. | |
| D859,625 S | 9/2019 | Yeats et al. | |
| D866,741 S | 11/2019 | Tran et al. | |
| D866,742 S | 11/2019 | Garcia et al. | |
| D866,744 S | 11/2019 | Gobber et al. | |
| 2015/0181855 A1* | 7/2015 | Willert | A01M 1/2022 239/34 |
| 2015/0202340 A1* | 7/2015 | Warberg Block | A61L 9/12 239/34 |
| 2016/0144064 A1* | 5/2016 | Santini | A01M 1/2044 239/6 |
| 2018/0353636 A1* | 12/2018 | Hafer | B05B 7/0081 |
| 2019/0336637 A1* | 11/2019 | Webster | A61L 9/042 |
| 2021/0379230 A1* | 12/2021 | Patton | A61L 9/122 |

\* cited by examiner

AIR FRESHENER WITH MULTIPLE AIR FLOW PATHS

This claims the benefit of U.S. Provisional Patent Application Ser. No. 63/109,894, filed Nov. 5, 2020 and hereby incorporated by reference in its entirety.

BACKGROUND OF THE INVENTION

This invention relates to air fresheners. More particularly, the invention relates to improved air fresheners for dispensing fragrant and/or deodorizing compositions in an enclosed area.

There is a desire to make the ambient air smell more pleasing in personal living spaces, professional office settings and in motor vehicles where the atmosphere within such confined spaces contains unpleasant odors from such things as smoking, cooking, pets and other common sources.

Air fresheners have been in use for many years. Devices for producing such a scent or fragrance are well known and have been extensively used indoors and in vehicles. Currently existing air fresheners typically consist of a fragrance delivery system. The majority of these delivery systems use a fragrant, volatilizable source which, when exposed to the atmosphere, delivers fragrance via evaporation. The rate determining step for these delivery systems is evaporation from the source.

Ficke's law teaches that the delivery rate from evaporation is dependent upon certain factors, including concentration and air flow. As such, these systems often deliver materials at an inconsistent rate, following first-order kinetics, due to the inconsistent air flow over the material which influences the rate of evaporation. This may lead to very high levels of fragrance initially and an unacceptably low level of fragrance after only a short period of time and eradicate or inconsistent fragrances depending upon the air flow across the material.

The ideal air freshener delivery system would follow zero-order kinetics and have a delivery rate constant over time and irrespective of the particular air flow over the material. This is difficult because perfumes typically have fifty to one hundred or more components, each with unique vapor pressures. The variation in vapor pressure causes each component to diffuse into the atmosphere at different rates.

Another disadvantage with many air freshener devices is that the fragrance-producing material is quickly depleted or consumed whereby a strong fragrance is generated for a short time. Furthermore, some prior devices have not been refillable, and therefore to maintain the emission of fragrance for a long period of time, it has been necessary to replace the entire device.

Various types of dispensing devices have been devised and used in which an aerosol material is intermittently discharged as a spray into a room by either a clock mechanism that forms a part of the device or an electrically operated valve that is also included as an integral part of the dispenser. One disadvantage of these devices is that the pressurized aerosol liquid and dispensers used therewith are relatively expensive, are bulky and provide only a periodic dispensing very high concentrations of fragrance for very short bursts.

Other prior devices utilize electrical heating for dispensing such materials as air fresheners and deodorizers. Such devices may often include a reservoir of liquid to be dispensed, an electric heater to warm the liquid to cause it to vaporize more readily, and an electrical plug to plug the device into an electric outlet or batteries to power the heater. These devices have very little to no control over the fragrance output, where the device continuously works as long as it receives electricity. The need for an electrical outlet or replacement of batteries is a significant detriment to such devices for practical application.

Volatile deodorizing agents have been utilized for years. These deodorants were dispensed from bottles, usually glass, which contained an absorbent wick which was mounted on a wire frame and which wick extended vertically down through the bottle, to the bottom thereof. When the bottle cap was removed, the end of the water frame became accessible and would be pulled up as much as desired, into the air to thereby expose a portion of the wick to the surrounding air. The liquid in the container by the wicking action of the wick, was raised to the top and evaporated into the air to thereby destroy offensive odors and to pleasantly scent the air as with the smell of pine trees. The time required to completely dispel an odor such as cigarette smoke in a given enclosed space, depended upon the extent of projection of the wick from the bottle. With such limited exposure, the amount of deodorant dispensed at any given time, was limited and thus, a long time was required to deodorize a given enclosed space.

One of the major problems of this type of deodorant is the fact that after the job was done, it was necessary for the user to remember to close the bottle so as not to waste the liquid through undesired volatilization. In addition, there is always the hazard that children, pets or even adults, could knock the bottle over, thereby spilling the liquid contents.

Gel formed products became available which would sublime in the presence of atmospheric air, to thereby release their active ingredients into the surrounding atmosphere. These products were constantly releasing their active ingredients by evaporation and/or sublimation. However, depending upon the intended application, it may be desirable to have even more distribution of the vaporized product throughout the environment, than is possible by merely exposing the gel at a fixed location with minimal or inconsistent air flow. Thus, in bathrooms which are subject to odor concentrations, the scent available from a sublimating gel or stick-like solid, may not be sufficient at any one time, to overcome an offensive bathroom odor.

Deodorant sprays offer the advantage of quick delivery, with very small particle size droplets which could immediately mask or neutralize an offensive odor. However, due to the problem with the fluorocarbons, it became necessary to do away with many such delivery systems.

Therefore, a need exists in the art for an air freshener system and method of fragrance delivery that does not suffer from these and other drawbacks with the prior art.

SUMMARY OF THE INVENTION

These and other shortcomings in the prior art have been addressed by this invention, which in various embodiments is an air-treating apparatus for dispensing a volatilizable material, such as air freshener fragrance, into the atmosphere of an enclosed area. The apparatus includes a canister with a cup therein housing and a reservoir of the volatilizable material. Multiple-configured air flow paths are arranged through the apparatus which enables air-flow therethrough in multiple configurations. The apparatus enables use of the consistent delivery rates of a volatilizable material producing a more consistent delivery rate than normally achieved with such devices.

The volatilizable material may be in the form of one or more rings with each ring having multiple spaced beads formed thereon. More than one ring may be stacked within the cup of the apparatus and each ring may have a different scent which in combination with the other rings in the cup delivers a pleasant environment. Moreover, the rings are such that a child or other person is not able to easily ingest them thereby offering a safety measure to the invention in various embodiments. Various configurations of the apparatus according to this invention may be mounted on a table or other horizontal surface or suspended from a wall or other convenient vertical surface.

In various embodiments, this invention is directed to an air freshener device that allows for consistent and reliable fragrance delivery from a supply of volatilizable material which may be replenished as needed. The volatilizable material is exposed to multiple airflow paths through the device so that the delivery of the fragrance is more consistent and not dependent upon a specific orientation of the device or exposure to a particular airflow stream.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 6 is an exploded view of the components of an alternative embodiment of this invention, which is adapted for mounting on a vertical surface, wall or the like.

DETAILED DESCRIPTION OF THE INVENTION

Figure 1:
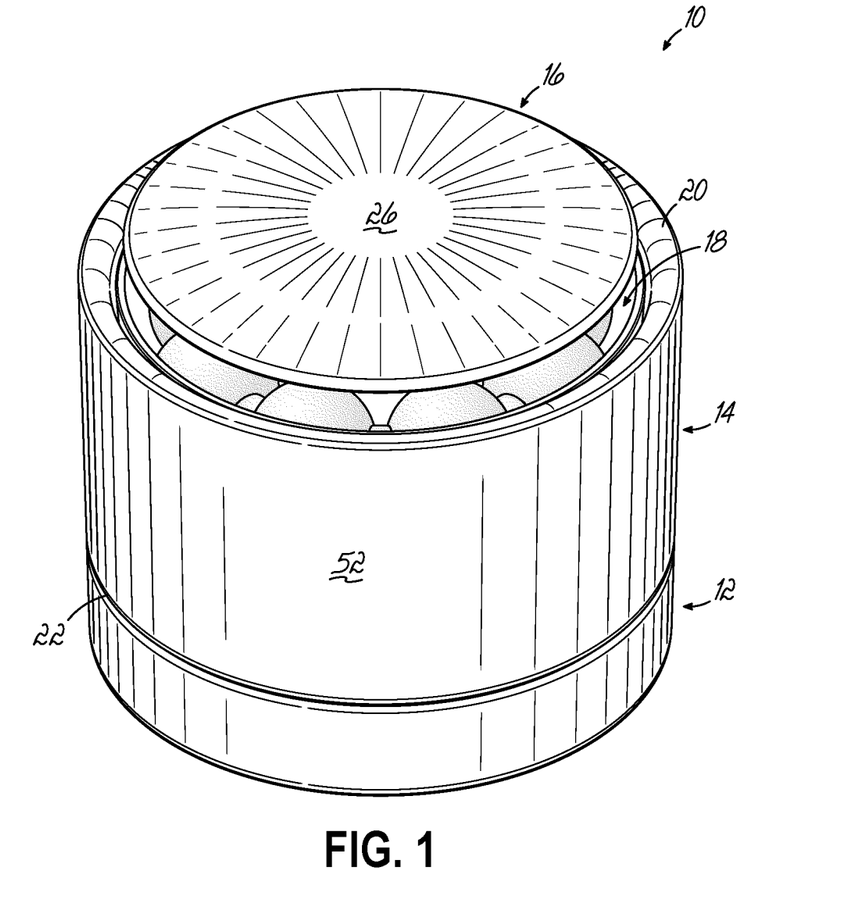
FIG. 1 is a perspective view of one embodiment of an air freshener apparatus according to this invention.

Referring to FIG. 1 an air freshener apparatus 10 according to one embodiment of this invention is shown. Components of the apparatus which are visible in FIG. 1 include a generally disc shaped base 12, a canister assembly which in one embodiment includes a cylindrical canister 14 and a cup 38. The canister assembly is supported on the base 12 and a lid 16 is mounted atop the canister 14. A gap 18 is provided around an outer periphery of the lid 16 relative to an upper edge 20 of the canister 14. In the embodiment shown in FIG. 1, the base 12 and the canister 14 each has a cylindrical outer shape of the same diameter with a seam 22 visible at a juncture between the base 12 and canister 14.

Figure 2:
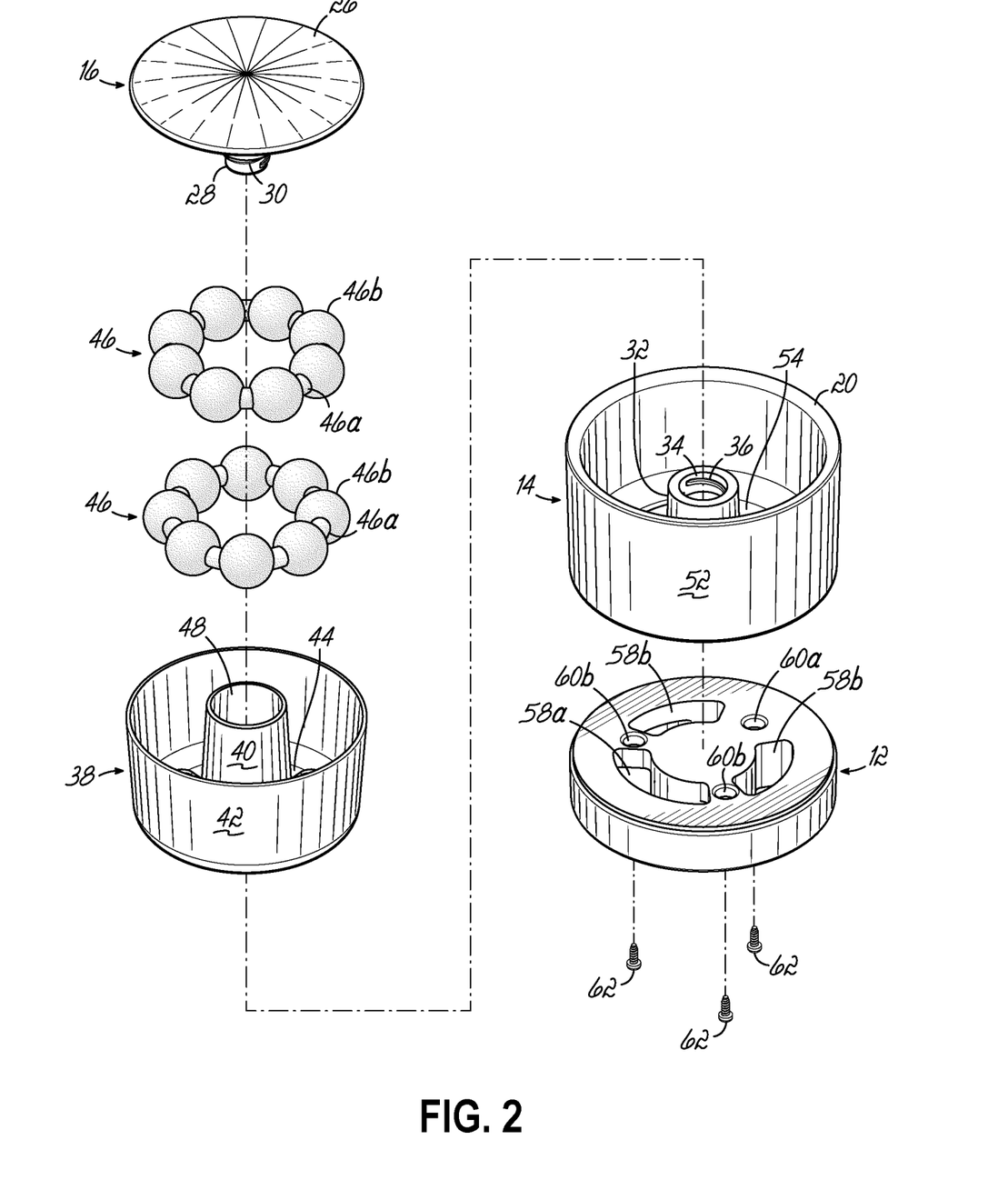
FIG. 2 is an exploded view of the air freshener apparatus of FIG. 1.
Figure 3:
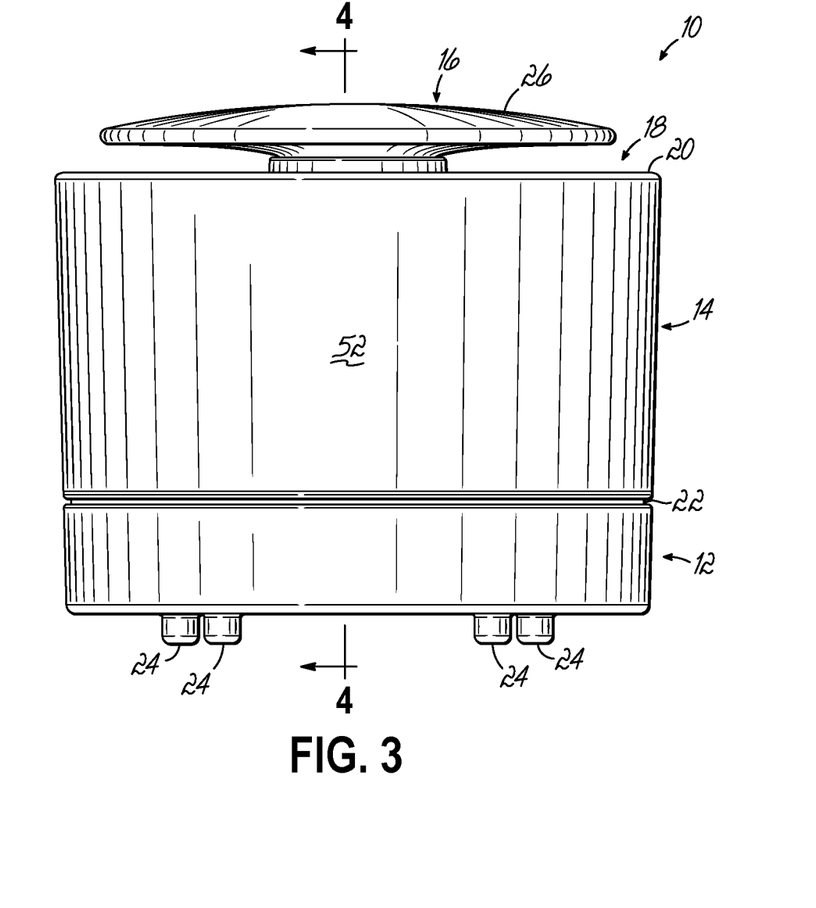
FIG. 3 is a side elevational view of the air freshener apparatus of FIGS. 1-2.
Figure 4:
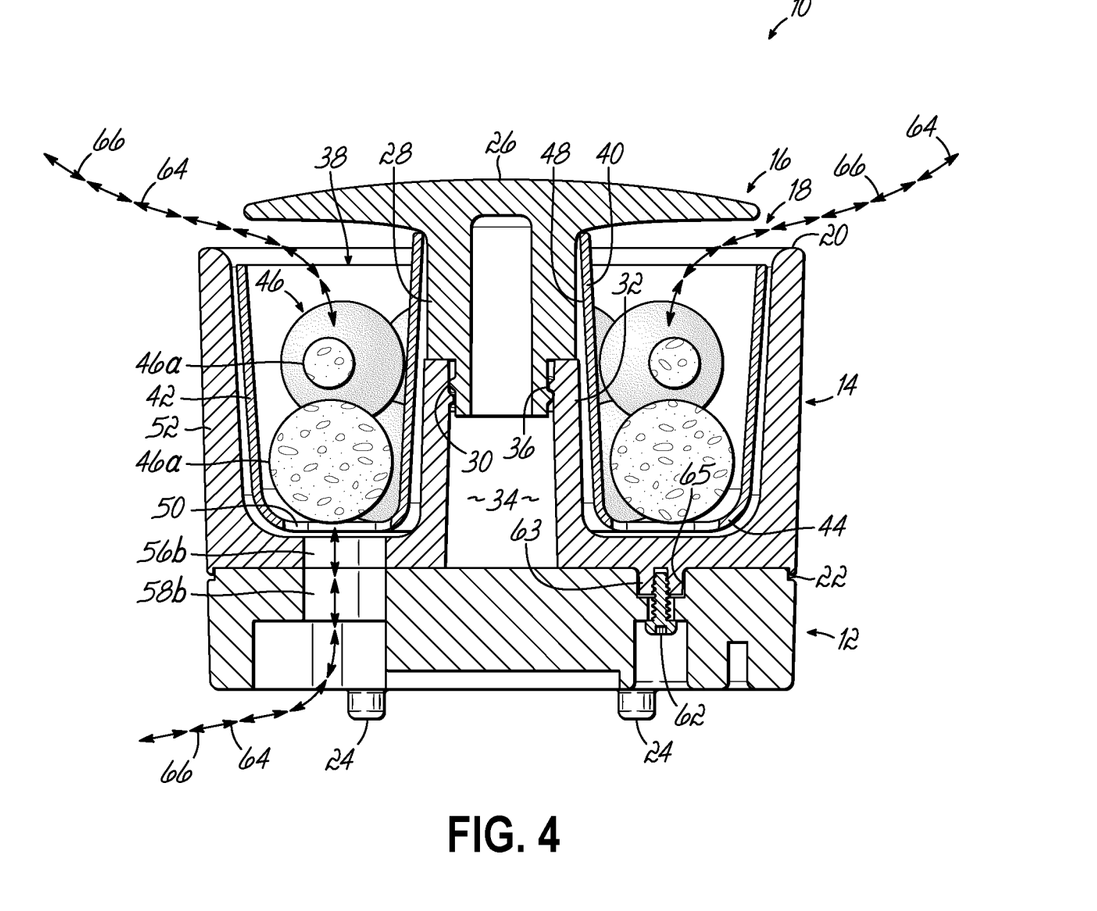
FIG. 4 is a cross-sectional view taken along line 4-4 of FIG. 3.

Additional components of the apparatus 10 are shown in FIG. 2 including a number of feet 24, three of which are shown in FIGS. 3-4, which are mountable to an underside of the base 12 to support the apparatus 10 on an underlying surface, table or the like (not shown). The feet 24 elevate the base 12 and the remainder of the apparatus 10 off of the underlying surface such that a spacing is provided between a bottom surface of the base 12 and the underlying surface (see FIGS. 3-4).

The lid 16 has an upper, circular, disc shaped top portion 26 and a stem 28 projecting downwardly from a center of the top portion 26. The stem 28 as an outer thread 30 traversing around its outer surface. The canister 14 has a central cylindrical post 32 extending upwardly. The post 32 has a central longitudinal hole 34 which includes a thread 36 adapted to mate with the thread 30 on the stem 28 of the lid 16. As such, the lid 16 is threadably mated with the canister 14 such that rotation of the lid 16 relative to the canister 14 raises or lowers the lid 16 relative to the canister 14 depending upon the direction of rotation. This rotation of the lid 16 increases or decreases the size of the gap 18 between the lid 16 and the canister 14 as desired by the user. In one embodiment, the gap 18 remains sufficiently limited so as to prevent someone from inserting their finger into the gap 18 and touching the contents of the apparatus 10.

The apparatus 10 according to this embodiment also includes a cup 38 situated between the canister 14 and the lid 16. The cup 38 has a central tubular member 40 and an outer circumferential sidewall 42 which are joined by a bottom wall 44. The stem 28 of the lid 16 extends downwardly through the tubular member 40 of the cup 38 to threadably mate with the post 32 of the canister 14. In the assembled device 10, aromatic and volatilizable or air freshener material 46 may be placed in the cup 38 or other deodorizing agents as desired by the user. In one embodiment of this invention, the cup 38 may be disposable such that when the aromatic material 46 is replenished a new cup 38 is used and the prior cup 38 disposed.

One embodiment of this invention is the aromatic material 46 which may include a ring 46a with spaced beads 46b protruding around the circumference of the ring 46a instead of individual beads arranged in the cup 38. This ring embodiment of the material 46 is aesthetically pleasing and also inhibits someone from ingesting an individual bead. Moreover, two rings of aromatic material 46 may be nested one upon the other for a compact arrangement in the cup 38. In some embodiments of this invention, one ring of material 46 may be of a first aromatic scent and the other ring may be of a complimentary, but different aromatic scent.

Figure 2A:
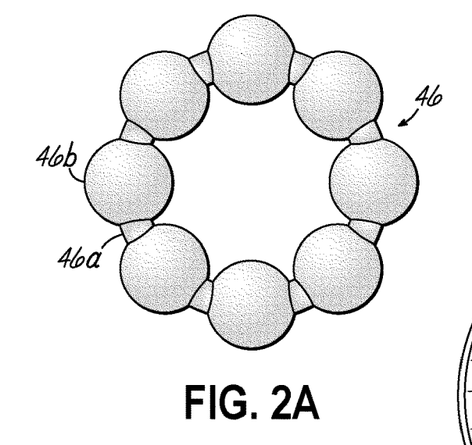
FIGS. 2A-2D are top plan views of components of the air freshener apparatus of FIGS. 1-2.
Figure 2B:
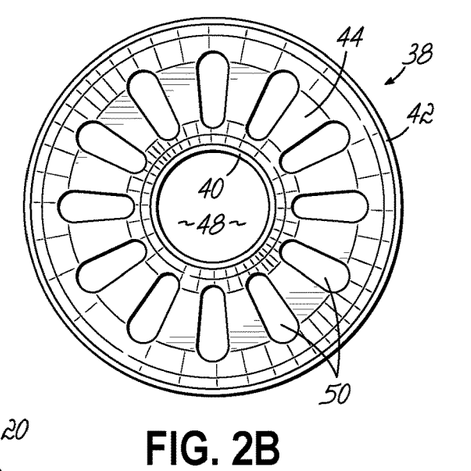

Referring to FIGS. 2A-2D, top plan views of the ring material 46, the cup 38, the canister 14 and the base 12 are shown, respectively. In FIG. 2A, the material 46 includes spaced individual beads 46b formed on the ring 46a. In FIG. 2B, a central conduit 48 is formed by the tubular member 40 of the cup 38. The bottom wall 44 of the cup 38 includes a number of radially oriented and generally oval open slots 50 arranged around the tubular member 40. The aromatic material 46 rests, in part, on the bottom wall 44 of the cup 38 and is directly exposed to the slots 50.

Figure 2C:
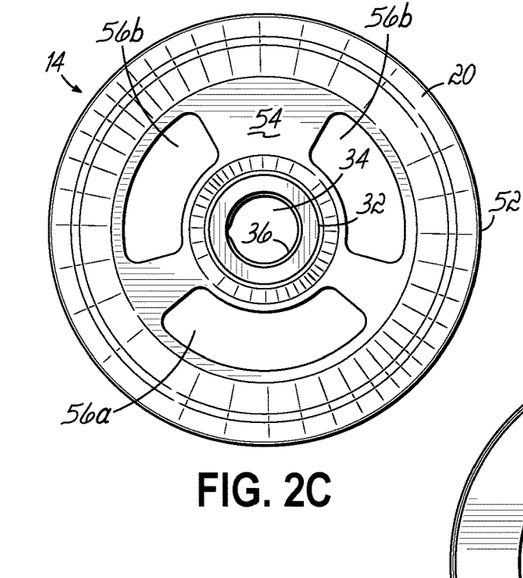
Figure 2D:
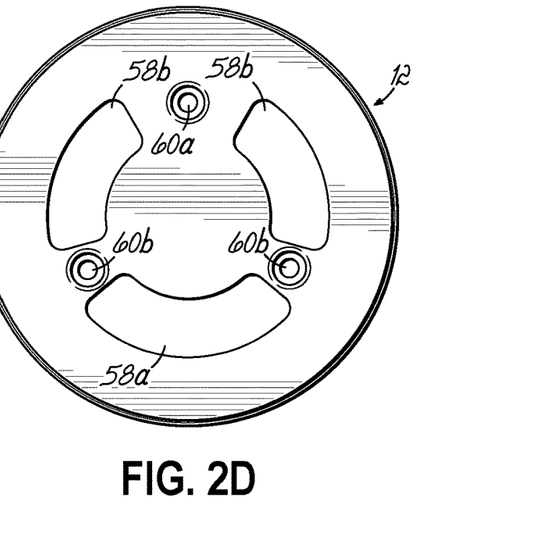

The canister 14 includes an upstand outer sidewall 52 extending circumferentially around the post 32 as seen in FIG. 2. In FIG. 2C, a bottom wall 54 of the canister 14 joining the post 32 to the sidewall 52 includes three are shaped apertures 56a, 56b arranged circumferentially around the post 32 and spaced from the adjacent aperture 56a, 56b. Three circumferentially arranged are spaced holes 58a, 58b are also formed in the base 12 and spaced from one another as shown in FIG. 2D. Three sockets 60a, 60b are also formed in the base 12, each of which is positioned between two adjacent holes 58a, 58b. The sockets 60a, 60b are equally spaced from one another at about 120° of separation. However, in one embodiment the holes 58a, 58b in the base are uniquely sized and positioned such that one of the holes 58a is larger than the other two holes 58b which are of equal size. The larger hole 58a is diametrically opposite one of the sockets 60a, 60b and the other two holes 58b are more closely positioned to the remaining sockets 60b as shown in FIG. 2D. The apertures 56a, 56b in the canister 14 may by sized and positioned similar to the holes 58a, 58b in the base 12 such that when the canister 14 is seated on the base 12, each aperture 56a, 56b is aligned with a corresponding hole 58a, 58b.

The sockets 60a, 60b each receive a screw 62 which may be screwed into the respective socket 60a, 60b and into the canister 14 to secure the components of the apparatus 10 together according to one embodiment of this invention (see FIG. 4). One or more bosses 63 may project downwardly from the canister 14 to mate with one or more recesses 65 in the base 12 to properly align the canister 14 on the base 12.

It will be appreciated by one of ordinary skill in the art that this invention is not limited to the number, shape, size, position and/or arrangement of openings such as the slots 50, apertures 56a, 56b, holes 58a, 58b and sockets 60a, 60b of any particular embodiment of the invention which is shown and described herein and other designs are within the scope of this invention.

One aspect of various embodiments of this invention is the air flow over the aromatic material 46 positioned in the cup 38. As shown most clearly in FIGS. 4 and 5, the aligned holes 58a, 58b and apertures 56a, 56b provide an upward flow path 64 from beneath the base 12 upwardly through the aligned holes 58a, 58b, apertures 56a, 56b and into the cup 38 through the slots 50 over the aromatic material 46 and out of the apparatus through the gap 18 and into the ambient environment to freshen the atmosphere. The feet 24 provide an offset for the base 12 relative to an underlying surface to allow for the airflow through the base 12.

Figure 5:
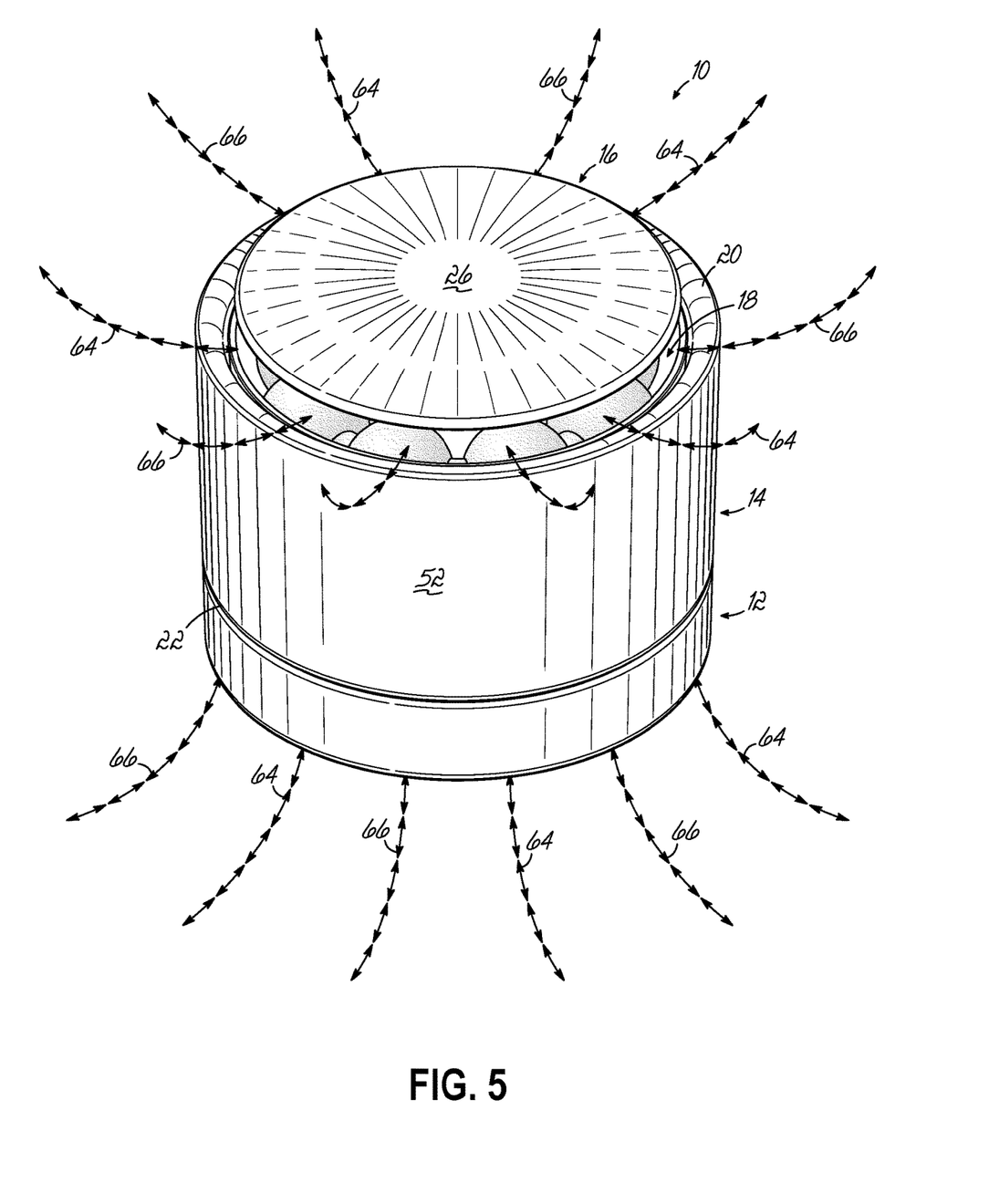
FIG. 5 is a perspective view of the air freshener apparatus of FIG. 1 schematically showing air flow paths out of the air freshener according to one aspect of this invention.

Additionally, the arrangement of the components of the apparatus 10 allows for a downward flow path 66 of air through the apparatus 10. Air may enter the apparatus 10 through the gap 18 around the lid 16 and downwardly into the cup 38 and over the material 46 and down through the slots 50 and out of the apparatus through the aligned apertures 56a, 56b and holes 58a, 58b and into the ambient environment to freshen the atmosphere. The dual directional flow paths 64, 66 provide for more even distribution of the air over the material 46 for consistent and regular dispersal of the aromatic material into the surrounding atmosphere. Moreover, if the apparatus 10 is placed in a location which is exposed to more air flow in one direction than the other, the fragrance generated by the material 46 is still distributed into the atmosphere. If an apparatus did not allow for multiple directional air flow paths, then its effectiveness would be limited if placed in an environment which was not compatible with the single air flow path. This limitation with such prior art air fresheners is overcome with various embodiments of this invention. Furthermore, the bi-directional air flow paths are provided with the apparatus 10 around the entire circumference of the apparatus 10.

Figure 6:
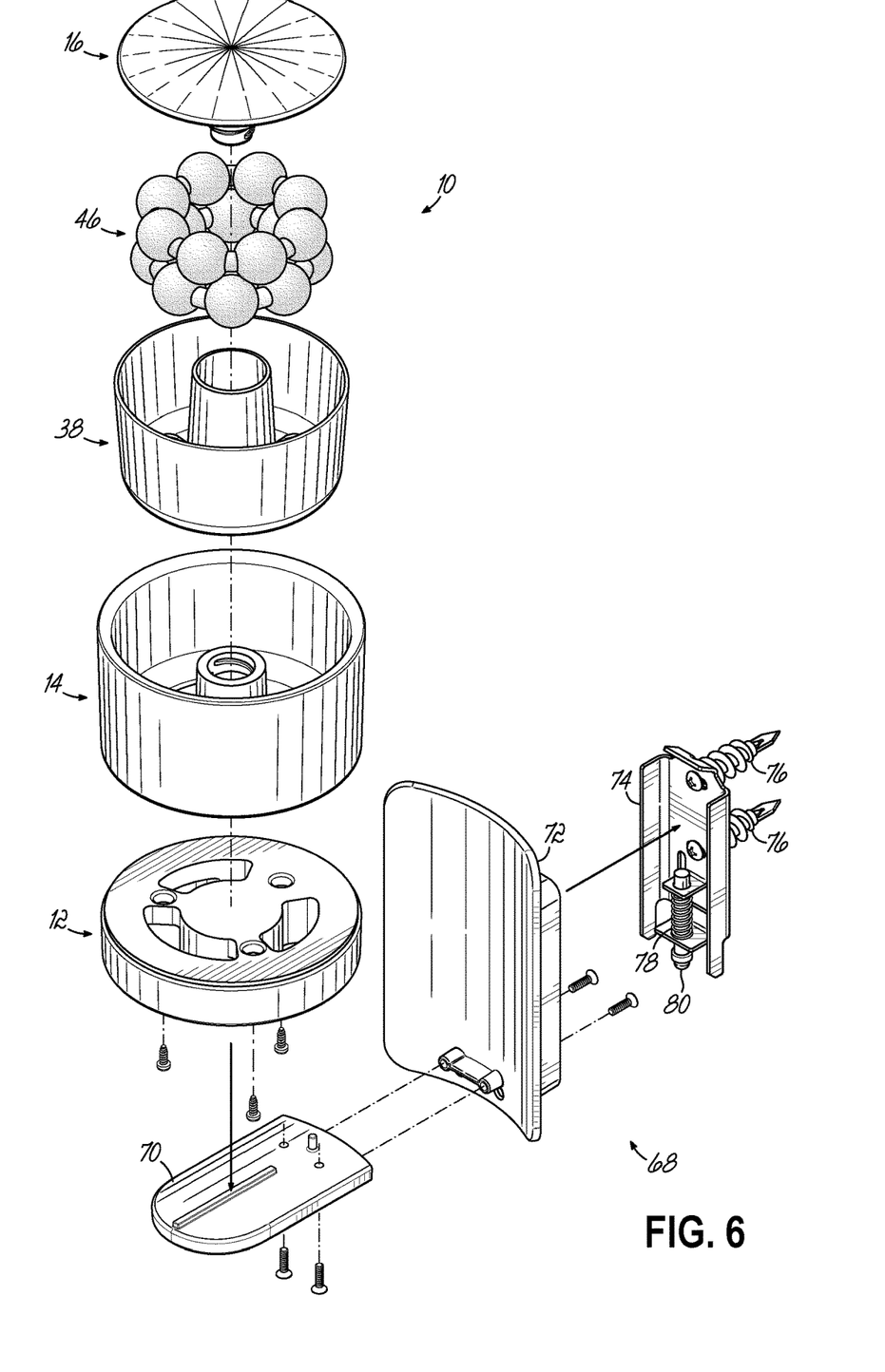

FIG. 6 shows an alternative embodiment of this invention in which the apparatus 10 is supported on a wall bracket assembly 68 including a supporting tongue 70, shield 72, mounting bracket 74 and anchors 76. A spring 78 and spring pin 80 allow for selective mounting of the shield 72 and tongue 70 to the mounting bracket 74 as desired.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:

1. An air freshener for containing an air freshener material, the air freshener comprising:
    a canister assembly having an open upper end in communication with a cavity adapted to hold the air freshener material;
    a lid coupled to the canister assembly to close at least a portion of the open upper end thereof; and
    a plurality of openings in the canister assembly in communication with the cavity and the air freshener material therein;
    wherein a plurality of air flow paths into and out of the cavity are provided for exposure of the air freshener material to a surrounding atmosphere of the air freshener, at least some of the plurality of air flow paths passing through selected ones of the plurality of openings and the open upper end of the canister assembly;
    wherein the canister assembly further comprises:
    a canister having a plurality of apertures in a bottom wall of the canister; and
    a cup seated within the canister and having a plurality of slots in a bottom wall of the cup;
    wherein the plurality of openings in the canister assembly are formed by combinations of the plurality of apertures and the plurality of slots.

2. The air freshener of claim 1 further comprising:
    a base supporting the canister assembly, the base having a plurality of holes therein in communication with the plurality of openings in the canister assembly and contributing to forming the plurality of air flow paths.

3. The air freshener of claim 1 wherein the canister assembly further comprises:
    a central post with the cavity being formed in an annular configuration about the post.

4. The air freshener of claim 3 wherein the lid further comprises:
    a downwardly directed stem threadably coupled to the central post for adjusting a position of the lid relative to the open upper end of the canister assembly and thereby modifying at least some of the plurality of air flow paths.

5. The air freshener of claim 4 wherein the lid has a generally circular shape.

6. The air freshener of claim 1 wherein the canister assembly has a generally annular shape.

7. The air freshener of claim 1 wherein a first portion of the plurality of air flow paths are directed upwardly through the canister assembly and a second portion of the plurality of air flow paths are directed downwardly through the canister assembly.

8. The air freshener of claim 1 further comprising:
    a wall bracket mounting assembly to support the air freshener, the wall bracket mounting assembly being adapted for mounting to a wall surface.

9. An air freshener for containing an air freshener material, the air freshener comprising:
    a generally annular canister assembly having an open upper end in communication with a cavity adapted to hold the air freshener material;
    a plurality of openings in the canister assembly in communication with the cavity and the air freshener material therein;
    wherein the canister assembly further comprises a canister having a plurality of apertures in a bottom wall of the canister and a cup seated within the canister and having a plurality of slots in a bottom wall of the cup;

wherein the plurality of openings in the canister assembly are formed by combinations of the plurality of apertures and the plurality of slots;

a generally circular lid coupled to the canister assembly to close at least a portion of the open upper end thereof;

wherein the canister assembly further comprises a central post with the cavity being formed in an annular configuration about the post;

wherein a plurality of air flow paths into and out of the cavity are provided for exposure of the air freshener material to a surrounding atmosphere of the air freshener, at least some of the plurality of air flow paths passing through selected ones of the plurality of openings and the open upper end of the canister assembly; and a base supporting the canister assembly, the base having a plurality of holes therein in communication with the plurality of openings in the canister assembly and contributing to forming the plurality of air flow paths.

10. The air freshener of claim 9 wherein the lid further comprises:

a downwardly directed stem threadably coupled to the central post for adjusting a position of the lid relative to the open upper end of the canister assembly and thereby modifying at least some of the plurality of air flow paths.

11. The air freshener of claim 9 wherein a first portion of the plurality of air flow paths are directed upwardly through the canister assembly and a second portion of the plurality of air flow paths are directed downwardly through the canister assembly.

12. The air freshener of claim 9 further comprising:

a wall bracket mounting assembly to support the air freshener, the wall bracket mounting assembly being adapted for mounting to a wall surface.

13. An air freshener combination comprising:

a canister assembly having an open upper end in communication with a cavity;

an air freshener material located within the cavity;

a lid coupled to the canister assembly to close at least a portion of the open upper end thereof; and a plurality of openings in the canister assembly in communication with the cavity and the air freshener material therein;

wherein a plurality of air flow paths into and out of the cavity are provided for exposure of the air freshener material to a surrounding atmosphere of the air freshener, at least some of the plurality of air flow paths passing through selected ones of the plurality of openings and the open upper end of the canister assembly, wherein a first portion of the plurality of air flow paths are directed upwardly through the canister assembly and a second portion of the plurality of air flow paths are directed downwardly through the canister assembly;

wherein the canister assembly further comprises:

a canister having a plurality of apertures in a bottom wall of the canister; and a cup seated within the canister and having a plurality of slots in a bottom wall of the cup;

wherein the plurality of openings in the canister assembly are formed by combinations of the plurality of apertures and the plurality of slots.

14. The air freshener combination of claim 13 further comprising:

a base supporting the canister assembly, the base having a plurality of holes therein in communication with the plurality of openings in the canister assembly and contributing to forming the plurality of air flow paths.

15. The air freshener combination of claim 13 wherein the canister assembly further comprises:

a central post with the cavity being formed in an annular configuration about the post;

wherein the air freshener material is formed in a ring shape surrounding the central post.

16. The air freshener combination of claim 15 wherein the lid further comprises:

a downwardly directed stem threadably coupled to the central post for adjusting a position of the lid relative to the open upper end of the canister assembly and thereby modifying at least some of the plurality of air flow paths.

17. The air freshener combination of claim 13 wherein the canister assembly has a generally annular shape and the air freshener material is formed in a ring shape.

18. The air freshener combination of claim 17 wherein the air freshener material further comprises:

a plurality of spaced beads;

a ring joining the plurality of spaced beads into the ring shape.

* * * * *